United States Patent
Gane et al.

(10) Patent No.: US 10,045,919 B2
(45) Date of Patent: Aug. 14, 2018

(54) CONTROLLED RELEASE ACTIVE AGENT CARRIER

(71) Applicant: Omya International AG, Oftringen (CH)

(72) Inventors: Patrick A. C. Gane, Rothrist (CH); Joachim Schölkopf, Oberkulm (CH)

(73) Assignee: Omya International AG, Oftringen (CH)

( * ) Notice: Subject to any disclaimer, the term of this patent is extended or adjusted under 35 U.S.C. 154(b) by 0 days.

(21) Appl. No.: 15/646,657

(22) Filed: Jul. 11, 2017

(65) Prior Publication Data

US 2017/0304165 A1 Oct. 26, 2017

Related U.S. Application Data

(62) Division of application No. 12/998,060, filed as application No. PCT/EP2009/062633 on Sep. 29, 2009, now Pat. No. 9,744,107.

(60) Provisional application No. 61/196,322, filed on Oct. 15, 2008.

(30) Foreign Application Priority Data

Sep. 30, 2008 (EP) ..................................... 08165543

(51) Int. Cl.
| | |
|---|---|
| *A61K 8/19* | (2006.01) |
| *A61K 9/14* | (2006.01) |
| *A61K 47/12* | (2006.01) |
| *A61Q 11/00* | (2006.01) |
| *A61Q 19/00* | (2006.01) |
| *A61K 8/11* | (2006.01) |

(52) U.S. Cl.
CPC .................. *A61K 8/19* (2013.01); *A61K 8/11* (2013.01); *A61K 9/145* (2013.01); *A61K 47/12* (2013.01); *A61Q 11/00* (2013.01); *A61Q 19/00* (2013.01); *A61K 2800/10* (2013.01); *A61K 2800/56* (2013.01)

(58) Field of Classification Search
CPC .... A61Q 19/00; A61Q 11/00; A61K 2800/56; A61K 2800/10; A61K 8/11; A61K 47/12; A61K 9/145; A61K 8/19
IPC .................. A61Q 19/00,11/00; A61K 2800/56, 2800/10, 8/11, 47/12, 9/145, 8/19
See application file for complete search history.

(56) References Cited

U.S. PATENT DOCUMENTS

| | | | |
|---|---|---|---|
| 3,357,790 A | 12/1967 | Saunders et al. | |
| 4,219,590 A * | 8/1980 | Shibazaki | C01F 11/185 106/419 |
| 4,379,168 A | 4/1983 | Dotolo et al. | |
| 4,678,662 A | 7/1987 | Chan | |
| 7,972,479 B2 | 7/2011 | Gane et al. | |
| 8,372,244 B2 | 2/2013 | Gane et al. | |
| 2004/0020410 A1 | 2/2004 | Gane et al. | |
| 2005/0074415 A1 | 4/2005 | Chow et al. | |
| 2006/0134013 A1 | 6/2006 | Sharma et al. | |
| 2006/0159753 A1 | 7/2006 | Ueki et al. | |
| 2006/0165583 A1 | 7/2006 | Makino et al. | |
| 2007/0280892 A1 | 12/2007 | Kindel et al. | |
| 2012/0321751 A1 | 12/2012 | Pedersen et al. | |

FOREIGN PATENT DOCUMENTS

| | | |
|---|---|---|
| EP | 2070991 A1 | 6/2009 |
| JP | 5964527 A | 4/1984 |
| JP | 07223813 A | 8/1995 |
| JP | 2002160918 A | 6/2002 |
| JP | 2003073117 A | 3/2003 |
| JP | 2008063291 A | 3/2008 |
| WO | 0039222 A1 | 7/2000 |
| WO | 04083316 A1 | 9/2004 |
| WO | 2008113838 A1 | 9/2008 |
| WO | 2008113840 A1 | 9/2008 |

OTHER PUBLICATIONS

Office Action dated Jul. 20, 2015 for CA 2,737,394.
Office Action dated Mar. 24, 2015 for IN 627/MUMNP/2011.
Office Action dated May 19, 2015 for EP 09 817 294.3.
Office Action dated Oct. 22, 2013 for JP 2011-529537.
Office Action for RU 2011117358/15.
Office Action dated Oct. 30, 2013 for KR Sep. 5, 2013-075014681.
Office Action for TW 098132632.
European Search Report dated Feb. 25, 2009 for EP 08165543.3.
Amr Edris, Pharmaceutical and Therapeutic Potentials of Essential Oils and their Individual Volatile Constituents: A Review, 21 Phytother. Res. 308 (2007).
Excerpt from Google Search Results re: Section IV: Assessment of Air Pollution Damage to . . . [downloaded Mar. 23, 2013] (Retrieved from internet for URL, see 101 rejection in office action).
Author unknown: Section IV, Assessment of Air Pollution Damage to Man-made Materials [downloaded Mar. 23, 2103] [retrieved from internet <URL:http://yosemite.epa.gov/ee/epa/eerm.nsf/vwAN/EE-0025-03.pdf/$file/EE-0025-03.pdf >]), excerpt provided (pp. 73, 83, 105-107), 5 pages.
Thomas et al. (Calcium sulfate: a review, J Long Term Eff Med Implants (2005), 15 (6):599-607, Abstract only), 1 page.
Industrial Minerals Assiciation—North America ("IMA-NA") (Calcium Carbonate [downloaded Mar. 24, 2013] [retrieved from internet <URL:http://www.ima-na.org/calcium-carbonate>]), 2 pages.
Memidex (Memidex dictionary/thesaurus, pyrophosphoric acid [downleaded Mar. 24, 2013] [retrieved from internet <URL:http://www.memidex.com/pyrophosphoric-acid >]), 5 pages.

(Continued)

*Primary Examiner* — Sean M Basquill
(74) *Attorney, Agent, or Firm* — Amster, Rothstein & Ebenstein LLP

(57) ABSTRACT

The present invention relates to carriers for the controlled release of active agents, comprising surface reacted natural or synthetic calcium carbonate, one or more active agents, wherein said one or more active agent is associated with said surface-reacted calcium carbonate, and wherein said surface-reacted natural or synthetic calcium carbonate is a reaction product of natural or synthetic calcium carbonate with carbon dioxide and one or more acids, wherein the carbon dioxide is formed in situ by the acid treatment and/or is supplied from an external source. It further relates to the preparation of loaded carriers, as well as their use in different applications.

20 Claims, 5 Drawing Sheets

(56) References Cited

OTHER PUBLICATIONS

The International Search Report for PCT/EP2008/062633.
The Written Opinion of the International Searching Authority for PCT/EP2008/062633.

* cited by examiner

CONTROLLED RELEASE ACTIVE AGENT CARRIER

This application is a divisional of U.S. application Ser. No. 12/998,060, filed May 20, 2011, which is the U.S. national phase of PCT Application No. PCT/EP2009/062633, filed Sep. 29, 2009, which claims priority to European Application No. 08165543.3, filed Sep. 30, 2008 and U.S. Provisional Application No. 61/196,322, filed Oct. 15, 2008, the content of which is hereby incorporated by reference.

The present invention relates to a carrier for the controlled release of active agents, a method of its preparation, and its uses.

Controlled release formulations are generally known in the art, especially with respect to pharmaceutical formulations. Such preparations are e.g. formulated to dissolve slowly and release a drug over time. The advantages of such sustained-release tablets or capsules are that they can be taken less frequently than instant-release formulations of the same drug, and that they keep levels of the drug steadier in the bloodstream. Sustained-release tablets are formulated so that the active ingredient is typically embedded in a matrix of insoluble substance, such as e.g. polyacrylic acids, so that the dissolving drug has to find its way out through the holes in the matrix.

Controlled release, however, can also mean immediate release under certain conditions, e.g. depending on the pH or the milieu at the destination environment.

Furthermore, such formulations are often coated with polymeric substances in order to ensure the release of active agent at the desired target environment. A typical example therefor are formulations for the oral administration being coated with a acid resistant, but alkali soluble coating, in order to ensure the passage through the stomach without loss of the active agent, and the subsequent slow or immediate release of the agent in the alkaline intestinal environment.

Controlled release formulations in the pharmaceutical field ideally are useful for various ways of administration, e.g.:
- oral application for the delivery of the agent to the intestines, where it is especially important that the agent is protected against the gastric acids while it is transported through the stomach prior to the delivery to the intestines,
- oral application for the delivery of the agent to the oral mucosa,
- inhalation of the carrier for delivery of the agent to the blood vessels (veins) lining the nasal passages, or
- dermal application of the carrier onto and through the skin.

However, controlled release formulations are also interesting in other fields, such as in agricultural, biological, cosmetic or any other technical applications, where it is important that the active agent is released at a specific target environment and is not released unless this environment is reached.

In any of such applications, useful controlled release formulation should meet the following requirements:
(i) retention of a sufficient quantity of active agent prior to the release at the target environment
(ii) release of a sufficient quantity of active agent at the target environment, and
(iii) sufficient protection by the carrier prior to delivery and release at the target environment so that it remains sufficiently active.

As mentioned above, this is usually achieved by complicated matrix or coating formulations involving time- and cost-intensive manufacturing processes.

Thus, there is a continuous need for new carriers allowing a controlled release of an active agent having the above-mentioned characteristics, which are easily available and processed and thus are more favorable than the known ones, not only from an economic point of view.

The above problem has been solved by a carrier for the controlled release of active agents, comprising:
- surface-reacted natural or synthetic calcium carbonate,
- one or more active agents,
- wherein said one or more active agent(s) is (are) associated with said surface-reacted calcium carbonate, and wherein said surface-reacted natural or synthetic calcium carbonate is a reaction product of natural or synthetic calcium carbonate with carbon dioxide and one or more acids, wherein the carbon dioxide is formed in situ by the acid treatment and/or is supplied from an external source.

Preferred synthetic calcium carbonate is precipitated calcium carbonate comprising aragonitic, vateritic or calcitic mineralogical crystal forms or mixtures thereof.

Preferably, the natural calcium carbonate is selected from the group comprising marble, chalk, calcite, dolomite, limestone and mixtures thereof.

In a preferred embodiment, the natural or synthetic calcium carbonate is ground prior to the treatment with one or more acids and carbon dioxide. The grinding step can be carried out with any conventional grinding device such as a grinding mill known to the skilled person.

Preferably the surface-reacted natural or synthetic calcium carbonate to be used in the present invention is prepared as an aqueous suspension having a pH, measured at 20° C., of greater than 6.0, preferably greater than 6.5, more preferably greater than 7.0, even more preferably greater than 7.5.

In a preferred process for the preparation of the aqueous suspension, the natural and synthetic calcium carbonate, either finely divided, such as by grinding, or not, is suspended in water. Preferably, the slurry has a content of natural or synthetic calcium carbonate within the range of 1 wt-% to 80 wt-%, more preferably 3 wt-% to 60 wt-%, and even more preferably 5 wt-% to 40 wt-%, based on the weight of the slurry.

In a next step, an acid is added to the aqueous suspension containing the natural or synthetic calcium carbonate. Preferably, the acid has a $pK_a$ at 25° C. of 2.5 or less. If the $pK_a$ at 25° C. is 0 or less, the acid is preferably selected from sulphuric acid, hydrochloric acid, or mixtures thereof If the $pK_a$ at 25° C. is from 0 to 2.5, the acid is preferably selected from $H_2SO_3$, $HSO_4^-$, $H_3PO_4$, oxalic acid or mixtures thereof. The one or more acids can be added to the suspension as a concentrated solution or a more diluted solution. Preferably, the molar ratio of the acid to the natural or synthetic calcium carbonate is from 0.05 to 4, more preferably from 0.1 to 2.

As an alternative, it is also possible to add the acid to the water before the natural or synthetic calcium carbonate is suspended.

In a next step, the natural or synthetic calcium carbonate is treated with carbon dioxide. If a strong acid such as sulphuric acid or hydrochloric acid is used for the acid treatment of the natural or synthetic calcium carbonate, the carbon dioxide is automatically formed. Alternatively or additionally, the carbon dioxide can be supplied from an external source.

Acid treatment and treatment with carbon dioxide can be carried out simultaneously which is the case when a strong acid is used. It is also possible to carry out acid treatment first, e.g. with a medium strong acid having a $pK_a$ in the range of 0 to 2.5, followed by treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably 1:0.05 to 1:5.

In a preferred embodiment, the acid treatment step and/or the carbon dioxide treatment step are repeated at least once, more preferably several times.

Subsequent to the acid treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or synthetic calcium carbonate as an aqueous suspension having a pH of greater than 6.0, preferably greater than 6.5, more preferably greater than 7.0, even more preferably greater than 7.5. If the aqueous suspension is allowed to reach equilibrium, the pH is greater than 7. A pH of greater than 6.0 can be adjusted without the addition of a base when stirring of the aqueous suspension is continued for a sufficient time period, preferably 1 hour to 10 hours, more preferably 1 to 5 hours.

Alternatively, prior to reaching equilibrium, which occurs at a pH greater than 7, the pH of the aqueous suspension may be increased to a value greater than 6 by adding a base subsequent to carbon dioxide treatment. Any conventional base such as sodium hydroxide or potassium hydroxide can be used.

Further details about the preparation of the surface-reacted natural calcium carbonate are disclosed in WO 00/39222 and US 2004/0020410 A1, wherein the surface-reacted natural calcium carbonate is described as a filler for paper manufacture, the content of these references herewith being included in the present application.

Similarly, surface-reacted precipitated calcium carbonate is obtained. As can be taken in detail from unpublished European Patent Application No. 07123077, surface-reacted precipitated calcium carbonate is obtained by contacting precipitated calcium carbonate with $H_3O^+$ ions and with anions being solubilised in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilised calcium ions correspond to an excess of solubilised calcium ions relative to the solubilised calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilised calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilised calcium ions.

In a preferred embodiment of the preparation of the surface-reacted natural or synthetic calcium carbonate, the natural or synthetic calcium carbonate is reacted with the acid and/or the carbon dioxide in the presence of at least one compound selected from the group consisting of silicate, silica, aluminium hydroxide, earth alkali aluminate such as sodium or potassium aluminate, magnesium oxide, or mixtures thereof. Preferably, the at least one silicate is selected from an aluminium silicate, a calcium silicate, or an earth alkali metal silicate. These components can be added to an aqueous suspension comprising the natural or synthetic calcium carbonate before adding the acid and/or carbon dioxide.

Alternatively, the silicate and/or silica and/or aluminium hydroxide and/or earth alkali aluminate and/or magnesium oxide component(s) can be added to the aqueous suspension of natural or synthetic calcium carbonate while the reaction of natural or synthetic calcium carbonate with an acid and carbon dioxide has already started. Further details about the preparation of the surface-reacted natural or synthetic calcium carbonate in the presence of at least one silicate and/or silica and/or aluminium hydroxide and/or earth alkali aluminate component(s) are disclosed in WO 2004/083316, the content of this reference herewith being included in the present application.

The surface-reacted natural or synthetic calcium carbonate can be kept in suspension, optionally further stabilised by a dispersant. Conventional dispersants known to the skilled person can be used. A preferred dispersant is polyacrylic acid.

Alternatively, the aqueous suspension described above can be dried, thereby obtaining the solid (i.e. dry or containing as little water that it is not in a fluid form) surface-reacted natural or synthetic calcium carbonate in the form of granules or a powder.

In a preferred embodiment, the surface-reacted natural or synthetic calcium carbonate has a specific surface area of from 5 $m^2/g$ to 200 $m^2/g$, more preferably 20 $m^2/g$ to 80 $m^2/g$ and even more preferably 30 $m^2/g$ to 60 $m^2/g$, measured using nitrogen and the BET method according to ISO 9277.

Furthermore, it is preferred that the surface-reacted natural or synthetic calcium carbonate has a weight median grain diameter of from 0.1 to 50 μm, more preferably from 0.5 to 25 μm, especially from 0.8 to 20 μm, most preferably from 1 to 10 μm, measured according to the sedimentation method. The sedimentation method is an analysis of sedimentation behaviour in a gravimetric field. The measurement is made with a Sedigraph 5100 of Micromeritics Instrument Corporation. The method and the instrument are known to the skilled person and are commonly used to determine grain size of fillers and pigments. The measurement is carried out in an aqueous solution of 0.1 wt-% $Na_4P_2O_7$. The samples were dispersed using a high speed stirrer and supersonicated.

In a preferred embodiment, the surface-reacted natural or synthetic calcium carbonate has a specific surface area within the range of 5 to 200 $m^2/g$ and a weight median grain diameter within the range of 0.1 to 50 μm. More preferably, the specific surface area is within the range of 20 to 80 $m^2/g$ and the weight median grain diameter is within the range of 0.5 to 25 μm. Even more preferably, the specific surface area is within the range of 30 to 60 $m^2/g$ and the weight median grain diameter is within the range of 0.7 to 7 μm.

The surface reacted calcium carrier is capable of associating and transporting an active agent. The association preferably is an adsorption onto the surface of the surface-reacted calcium carbonate particles, be it the outer or the inner surface of the particles or an absorption into the particles, which is possible due to their porosity. In this respect, it is believed that because of the intra and interpore structure of the surface reacted calcium carbonate, this material is a superior agent to deliver previously ad/absorbed materials over time relative to common materials having similar specific surface areas.

Thus, the ad/absorption characteristics can be controlled by the pore size and/or pore volume and/or surface area for a given agent.

Preferably, the surface-reacted natural or synthetic calcium carbonate has an intra-particle porosity within the range of from 5 vol.-% to 50 vol.-%, preferably of from 20 vol.-% to 50 vol.-%, especially of from 30 vol.-% to 50 vol.-% calculated from a mercury porosimetry measurement. From the bimodal derivative pore size distribution curve the lowest point between the peaks indicates the diameter where the intra and inter-particle pore volumes can be separated. The pore volume at diameters greater than this diameter is the pore volume associated with the inter-particle pores. The total pore volume minus this inter particle pore volume gives the intra particle pore volume from which the intra particle porosity can be calculated, preferably as a fraction of the solid material volume, as described in *Transport in Porous Media* (2006) 63: 239-259.

Thus, the intra-particle porosity determined as the pore volume per unit particle volume is within the range of from 20 vol.-% to 99 vol.-%, preferably from 30 vol.-% to 70 vol.-%, more preferably from 40 vol.-% to 60 vol.-%, e.g. 50 vol.-%.

As already mentioned ad/absorption and release of the active agent is essentially controlled by the pore size, which preferably is in a range of from 10 to 100 nm, more preferably in a range of between 20 and 80 nm, especially from 30 to 70 nm, e.g. 50 nm.

Thus, generally, any agent fitting into the intra- and/or inter particle pores of the surface-reacted calcium carbonate carrier is suitable to be transported by the surface-reacted calcium carbonate carriers according to the invention.

Within these ranges any active agent, be it for the transport in or into the human or animal body, in agricultural or any other applications, can be useful in the present invention, e.g. agents selected from the group comprising pharmaceutically, biologically, cosmetically active agents, scented agents or flavoring agents, biocides, pesticides or herbicides, and disinfecting agents.

For example, active agents such as those selected from the group comprising triclosan, anticarcinogens, limonene, peppermint, surfactants like defoamers, or softeners, mineral oils, silicone, wetting agents, wax, paraffin, hydrolytic agents such as hydrolytic binders, anti-dusting oils, and o-phenylphenol and Bronopol can be used.

An especially interesting group of active agents are anticarcinogens, as cancer cells are acidic, and this acidity assists the release of the anticarcinogen at the cancer cells.

If the target environment is the human or animal body, the carriers having an active agent associated therewith according to the invention can be administered directly via the oral way, via inhalation, and via the dermal tissue as mentioned above. They can even be administered via injection to the body, e.g. intravenously or subcutaneously. If sufficient agent is delivered to the target environment, the present invention may even provide an alternate route to providing agents via vaccination.

In a preferred embodiment the surface-reacted calcium carbonate carrier may be combined with one or several further carrier materials, such as for example a chewing gum or tooth paste formulation as regards the oral administration.

Thus, in a preferred embodiment, a tooth paste comprising surface-reacted calcium carbonate as a carrier of, e.g. triclosan, or flavoring agents can be provided.

In the case where the active agent is to be transported into the intestines, the carrier having the active agent associated therewith can be formulated into common galenical formulations such as oil-based capsules such as vitamin capsules, tablets, creams and the like.

In the case of inhalation applications, the carrier may be combined with, e.g. a nasal spray formulation, transporting pharmaceutically active agents, or odorous substances including scented oils such as limonene or peppermint.

Dermal application may be formulated e.g. into a cosmetic formulation which may be applied to the skin or hair. Generally any kind of cosmetic formulations are suitable such as patches, soaps, creams such as skin creams and sunscreens, foundations, hair care products, perfumes, powders such as foot powders or facial powders, lipsticks, deodorants, or bath additives, e.g. in the form of bath bombs or bath tablets, wherein natural oils such as peppermint oil or amaranth oil may be incorporated.

Also, it is possible to use the surface-reacted calcium carbonate suspended in oils such as mineral oil fractions or vegetable oils such as jojoba oil or in alcohols such as ethyl alcohol.

As can be seen from the above the surface-reacted calcium carbonate carrier is useful to transport various agents associated therewith.

There are, however, some limitations, which therefore are excluded from the subject-matter of the present invention. Thus, agents reacting with the surface-reacted calcium carbonate such as acidic agents sometimes are not suitable to be transported with the surface-reacted calcium carbonate. On the other hand, even acidic agents may be advantageously used, e.g., if the calcium salt of the acidic agent is required or beneficial. A certain level of acidity can also enhance adsorption to the surface of the carrier.

The delivery mechanism, following ab/adsorption of the agent onto and/or into the surface-reacted calcium carbonate is essentially based on one or several of the following mechanisms:

1. by diffusion out of tablet or a similar macroscopic body formed out of surface-reacted calcium carbonate particles (slow, continuous release)
2. by diffusion out of discrete particles of surface-reacted calcium carbonate particles, be it in the form of a powder or a suspension (medium slow, continuous release)
3. by destruction of the tablet or a similar macroscopic body formed out of surface-reacted calcium carbonate particles, for example by application of a mechanical force on the tablet (chewing)(release first slow, then medium slow)
4. A special case is given by the situation when the surface-reacted calcium tablet is loaded with a hydrophobic agent such as an oil and the tablet is then immersed in a polar fluid such as water. There is a rapid disintegration observed due to the invading pressure of the water.

5. By destruction of the surface-reacted calcium particle structure itself Destruction could take place (fast, localized release as soon as particle structure decays);

The association, i.e. ad/absorption of the agent onto and/or into the surface-reacted calcium carbonate carrier is generally effected by contacting the surface reacted calcium carbonate with a solution or suspension of the active agent in a suitable medium, which is preferably water, but can generally be any medium. However, if the medium is acidic, it needs to be weaker than the acid that formed the reacted surface salt and in dilute form. Then it can be exposed to a low pH for a limited time at least.

For this purpose, the surface-reacted calcium carbonate may be in the form of a tablet or powder, which after the association is completed is separated from the excess liquid, solution or suspension, e.g. by filtration, and optionally dried.

The resulting loaded tablet or powder is applied directly or combined with a second carrier as described above, such as a cream, a tablet, capsule or any other galenical form as described above according to methods well-known in the art.

With respect to the drying of the surface reacted calcium carbonate, it is preferred to apply a well controlled drying method, such as gentle spray drying or oven-drying.

The following figures, examples and tests will illustrate the present invention, but are not intended to limit the invention in anyway.

EXAMPLES

Example 1

Release Characteristics

For comparing the release characteristics of the carrier according to the invention a tablet of surface reacted calcium carbonate was formed, as well as of a silica reference product featuring a similar high surface area as the surface-reacted calcium carbonate.

Preparation of Surface-Reacted Calcium Carbonate

The surface-reacted calcium carbonate was prepared in a 100 litre ESCO-reactor.

8000 g of dry natural calcium carbonate having a d50 of 0.7 µm (Sedigraph) (64 wt.-%<1 µm) was filled into the vessel. Then water was added until a solids content of 10 wt.-% was obtained. The resulting slurry was heated to 70° C., then 3733 g of phosphoric acid (=35 wt.-% dry/dry) was added during 90 minutes at a solids content of 75 wt.-%, under stirring with an anchor stirrer at 50 rpm and a disc stirrer at 2000 rpm. 30 minutes after the completion of the addition the temperature was decreased and the slurry upconcentrated in a filter press.

Figure 1:
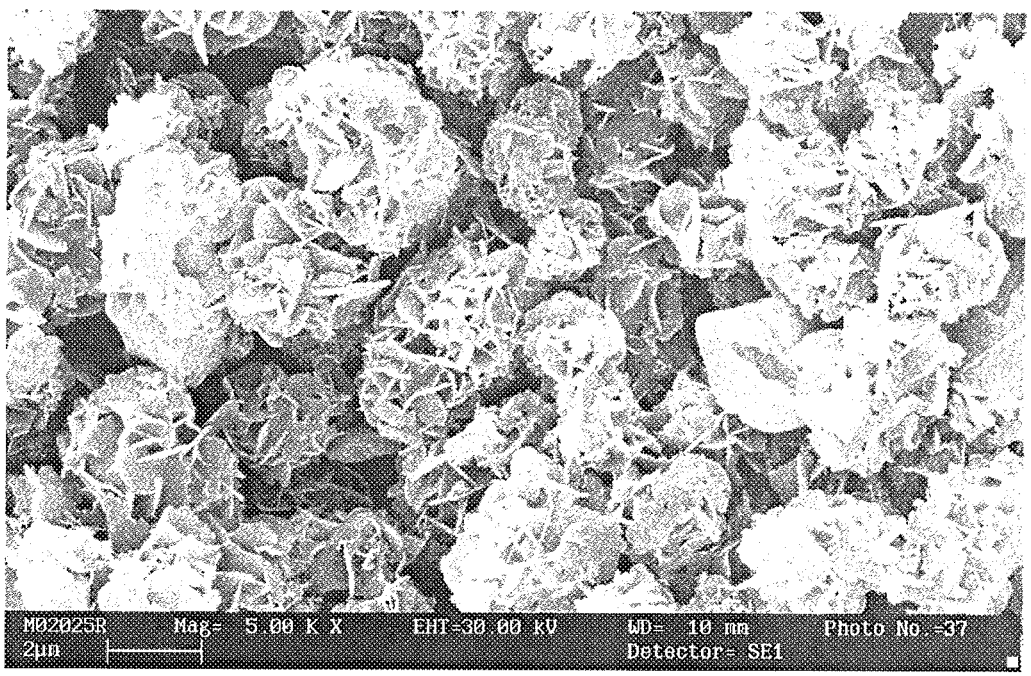
FIG. 1 shows a SEM image of surface-reacted calcium carbonate useful in the present invention

The surface-reacted calcium carbonate used in the following example had a number mean particle size $d_{50}$ (Sedigraph) of 3 µm a rose-like surface structure as can be taken from FIG. 1 a pH of 7.5 to 9.5 a specific surface area as measured by BET: 60 $m^2/g$

Preparation of Surface-Reacted Calcium Carbonate Tablets

Figure 2:
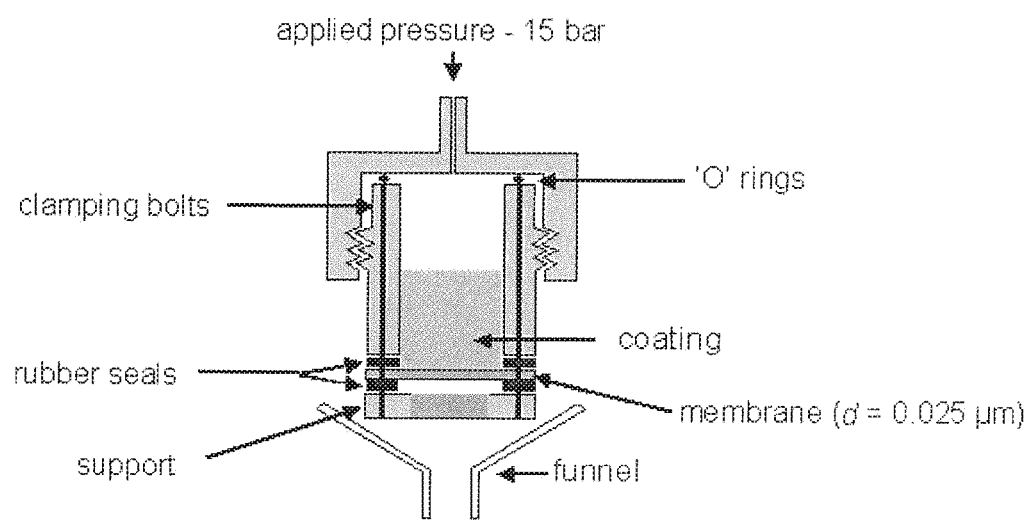
FIG. 2 shows an apparatus designed and suitable for making surface-reacted calcium carbonate tablets from wet suspensions.

The tablet was made from a suspension of surface-reacted calcium carbonate having a solids content of 30 wt-%±5 wt.-%. The tablets were formed by applying a constant pressure to the suspension for several minutes, typically 1-10 min, such that water is released by filtration through a fine 0.025 µm filter membrane resulting in a compacted tablet of the surface-reacted calcium carbonate. The apparatus used is illustrated in FIG. 2. It is further described in: Ridgway, C. J., Gane, P. A. C. and Schoelkopf, J., "Modified Calcium Carbonate Coatings with Rapid Absorption and Extensive Liquid Uptake Capacity", Colloids and Surfaces A, 236(1-3), 2004, p. 91-102.

The tablets were removed from the apparatus and dried in an oven at 80° C. for 24 hours.

Preparation of Reference Tablets

The silicates used as a reference were products available under the tradename GASIL® HP39 and P101 available from INEOS Silicas and had the following characteristics:

|  | GASIL ® HP39 | GASIL ® P101 |
| --- | --- | --- |
| Pore volume | 1.8 ml/g | 1.1 ml/g |
| Average particle size (Malvern) | 10.3 µm | 10.0 µm |
| Oil absorption | 280 g/100 g | 200 g/100 g |
| pH | 7.0 | 7.0 |
| SSA (BET) | 260 $m^2/g$ | 363 $m^2/g$ |

Figure 3:
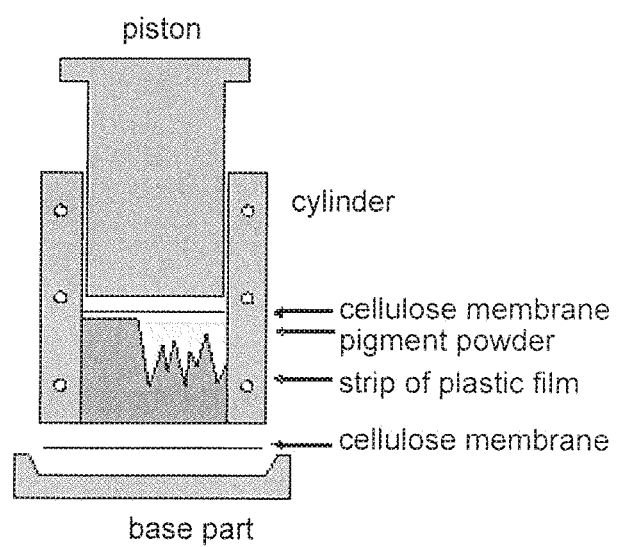
FIG. 3 shows a schematic cross-section of a die used for compacting powders.

The silicate powders were formed into tablets in the form of blocks by a dry compaction method as follows:

For the preparation of the pigment blocks a cylindrical hardened steel die attached to a base plate with a single acting upper piston was used which is suitable for a wide range of particle sizes, chemistries and morphologies. The die is divisible into two parts to aid removal of the compacted pigment sample and the walls of the die are protected with a strip of plastic film to prevent sticking of the powder to the wall and to reduce edge friction (FIG. 3).

Further details of the method for producing such kind of tablet blocks can be taken e.g. from Pennanen M., "Methods for producing and testing tablets of dry pigments and coating colors", Research report, Abo Akademi, Turku and OMYA, Oftringen, 1996; Ridgway C. J., Ridgway K., Matthews G. P., "Modelling of the void space of tablets compacted over a range of pressures", J. Pharm. Pharmacol. 49, (1997), p. 377; and: 658458.1

Gane, P. A. C., Schoelkopf, J., Spielmann, D. C., Matthews, G. P., Ridgway, C. J., "Fluid Transport into Porous Coating Structures: Some Novel Findings", Tappi Journal, 83(5), 2000, p. 77-78.

Association of Active Agent

The surface-reacted calcium carbonate tablets, which were previously ground to a cubic shape, as well as the silicate blocks were placed in dishes. Limonene (pure or in alcohol/water) was added to the dishes such that the top surfaces of the tablets remained in contact with air (allowing any air in the tablets to escape as limonene is absorbed).

Wetting continued for an additional 12 hours following the visual observation that the surfaces of the cubes and blocks are wetted by the limonene.

The tablets were removed from the dish and allowed to stand in an open environment under standard temperature and pressure conditions until limonene could not be detected by smelling any more (for up to 350 hours). At this point, the tablets were placed in a closed jar and heated in order to analyze the weight of remaining limonene.

Figure 4:
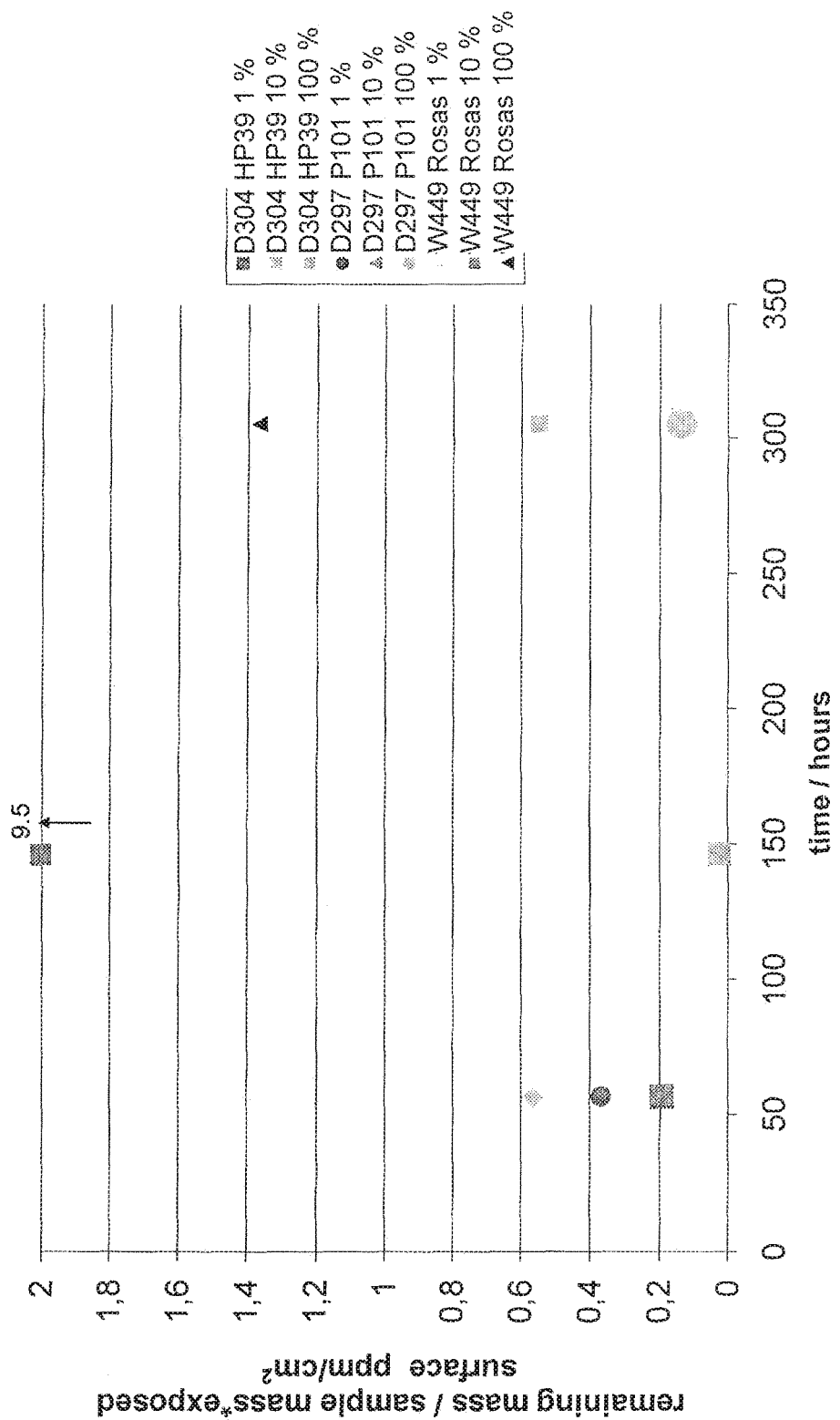
FIG. 4 shows a graph illustrating the release characteristics of a carrier according to the invention and a comparative sample.

In all cases, surface reacted calcium carbonate provided for a slower release of limonene than silica (FIG. 4; The percentages given refer to wt.-% limonene in ethyl alcohol; W449 refers to limonene loaded surface reacted calcium carbonate according to the invention, D 304 refers to limonene loaded HP 39 silicate; D 297 refers to limonene loaded P101 silicate as described above).

The quantification was carried out by gas chromatography in a HS TurboMatrix 40 Trap Perkin Elmer using the following parameters:

Temp. Mode: Oven 90° C., Needle 100° C., Transfer 110° C., Trap Low 40° C., Trap High 280° C.

Timing: Thermo 20.0 min, Delay: 0.8 min, Pressurize 1.0 min, Dry Purge 5.0 min,

Desorb. 0.1 min, Trap Hold 5.0 min

Column: 101 kPa, Vial: 101 kPa, Desorb: 101 kPa GC Method AutoSystem XL Perkin Elmer Column: Optima 5 MS 1.0 μm, 50 m*0.32 mm, Macherey-Nagel Injector 130° C., Split on Temp.: 130° C. 1.0 min, 10° C./min to 220° C. 0.0 min Pressure: 70 kPa MS Turbo Mass Perkin Elmer Solvent Delay 4.5 min Full Scan 25 to 300 (EI+)

Calibration: 0.0200 g Limonene/100 ml EtOH 0.0517 g Limonene/50 ml EtOH 0.1050 g Limonene/50 ml EtOH 0.2394 g Limonene/50 ml EtOH 0.7597 g Limonene/50 ml EtOH 0.5 μl injected in a HS vial (0.100 μg/0.517 μg/1.050 μg /2.394 μg/7.597 μg Limonene)

Korrelation $r^2$: 0.9994

Example 2

Transport and Release of Oily substances in an Aqueous Environment

For illustrating the properties of the carrier according to the present invention with respect to the transport and release of oily substances in an aqueous environment, bath bombs and bath tablets were produced with surface-reacted calcium carbonate saturated with scents (natural oils) such as amaranth as well as peppermint oil. The bath bombs or bath tablets were dropped into water at a temperature of 37° C. in order to extract and evaluate the released oil.

1. Bath bombs a) Material

Surface-reacted calcium carbonate: prepared as described under Example 1 above

Natural oil: Amaranth oil

Additives: Citric acid

Sodium bicarbonate

Hamamaelis water witch hazel

Colour Vitasin Patentblue (Clariant)

Food coloring red

Food coloring yellow

Solvent: n-Heptane b) Compositions

|  | Sample 1 | Sample 2 | Sample 3 |
|---|---|---|---|
| Citric acid | 100.123 g | 100.102 g | 100.250 g |
| Sodium bicarbonate | 200.037 g | 200.245 g | 200.030 g |
| Colour | 3 drops colour red | 5 drops colour brown | 0.016 g |
| Witch hazel water | approx. 2.5 to 3 g | approx. 2 to 2.5 g | 2.212 g |
| Surface-reacted calcium carbonate |  | 30.056 g |  |
| Oil | Amaranth | Amaranth 9.9599 g | Amaranth |
| Surface-reacted calcium carbonate saturated with oil | 12.304 g (of 7.7 g surface-reacted calcium carbonate saturated with 5.55 g oil) |  | 20.4053 g (of 17.32 g surface-reacted calcium carbonate saturated with 5.36 g oil) |
| Calculated content of oil | 1.8 wt-% | 2.9 wt-% | 1.7 wt-% | c) Preparation of the Bath Bombs

Citric acid and sodium bicarbonate were provided and well blended manually in a mortar. The colour solutions were added and well mixed. Subsequently, the given amounts of surface-reacted calcium carbonate and amaranth oil were added, either by adding the surface-reacted calcium carbonate saturated with the amaranth oil and manually well mixed (sample 1 and 3), or by adding the components separately (sample 2). Onto these batches witch hazel was sprayed (with a squirt bottle) while stirring manually. As soon as the batch sticks together upon squishing, potions of the bulk are put into a conventional aluminium form.

Any one of the resulting bombs was dried over night at room temperature. Then, each bomb was put into a 2000 ml beaker filled with 1000 ml tap water at approx. 37° C.

After the resulting suspension (amaranth) had cooled down to less than 30° C. (in approx. 30 to 40 min.), the whole contents were extracted with heptane in a separation funnel.

The water phase (pH 6.6±0.2) was discarded; the oil/solvent phase was filled into a 50 ml brown glass bottle and analyzed by determining the weight after evaporation of the solvent. The appearance of the solvent phases is turbid, milky white for the amaranth sample.

d) Results and Discussion

|  | Weight bath bomb | Calculated oil content in wt-% | Calculated oil content in mg | Content recovered in mg | Content recovered in wt-% |
|---|---|---|---|---|---|
| Sample 1a | 24.2545 g | 1.8 wt-% | 437 mg | 344 mg | 78.8 wt-% |
| Sample 1b | 12.5365 g |  | 226 mg | 180 mg | 79.8 wt-% |
| Sample 2a | 27.4791 g | 2.9 wt-% | 797 mg | 356 mg | 44.7 wt-% |
| Sample 2b | 31.1058 g |  | 902 mg | 322 mg | 35.7 wt-% |

It can be taken from the above table that it is more favourable to saturate the calcium carbonate with the oil instead of just mixing it, wherein the recovery rate in samples 1a and b are very high confirming the good performance of the present invention with respect to the release of oily substances in an aqueous environment.

2. Bath Tablets
a) Material
Surface-reacted calcium carbonate: prepared as described under Example 1 above
Natural oils: Amaranth oil
Additives: Citric acid
   Sodium bicarbonate
   Hamamaelis aqua witch hazel
Solvent: n-Heptane
b) Preparation of the Bath Tablets
Sample 4:
55 wt-% of a citric acid/sodium bicarbonate mixture (in a weight ratio of 1:2) were manually blended with 10 wt-% amaranth oil in a mortar. 35 wt-% of surface-reacted calcium carbonate were added in order to obtain a powdery batch.
Sample 5:
35 wt-% of surface-reacted calcium carbonate were manually mixed with 10 wt-% amaranth oil in a mortar. The mixture was then added to 55 wt-% of a citric acid/sodium bicarbonate mixture (in a weight ratio of 1:2) and manually mixed in order to obtain a powdery batch.
Sample6:
34.5 wt-% of surface-reacted calcium carbonate were manually mixed with 10 wt-% amaranth oil in a mortar. The mixture was then added to 54.5 wt-% of a citric acid/sodium bicarbonate mixture (in a weight ratio of 1:2) and manually mixed in order to obtain a powdery batch. While squishing manually, 2 wt-% of Hanmamelis water witch hazel was sprayed onto the batch in order to get a sticky powder.

From each of these samples tablet structures were formed by using a cylindrical hardened steel die attached to a base plate with a single acting upper piston. The die is divisible into two parts to aid removal of the compacted powder sample and the walls of the die are protected with a strip of plastic film to prevent sticking of the powder to the wall and to reduce edge friction. Additionally, the powders were covered with a cellulose membrane at the bottom as well as on top before being compacted in a hydraulic press for 1 minute at a predetermined force of 75 kN (an effective pressure of 35 bar). The tablets were formed of 1.5 to 1.8 cm in height and a diameter of 4.8 cm. All tablets were well compacted.

The height of the powder in the instrument was approximately 4.5 to 5 cm (the maximum height of the cylindrical steel is 8 cm).
c) Results and Discussion
Subsequently, 10 g of each tablet were dissolved in tap water at 37-38° C. The dissolution took about 6 minutes for samples 4 and 5 and more than 6 minutes for sample 6.

Example 3

Transport and Release of Oily Substances in an Oily Environment

For illustrating the properties of the carrier according to the present invention with respect to the transport and release of oily substances in an oily environment, as it is often present in cosmetic formulations, a formulation of surface-reacted calcium carbonate was compared with a formulation of non surface-reacted calcium carbonate.
a) Material
Surface-reacted calcium carbonate: prepared as described under Example 1 above
Commercially available non surface-reacted calcium carbonate (Omyacarb 2 of OMYA AG)
Commercially available methylbutyl isovalerat
Hexadecane
GC-MS:—Before GC-MS analysis, the samples were 21.25× diluted in hexadecane
   (80 µl sample and 1620 µl solvent)
   GC Method AutoSystem XL Perkin Elmer
   Column: Optima 5 MS 1.0 µm, 50 m*0.32 mm, Macherey-Nagel
   Injector 300° C., Split on
   Temp.: 220° C. 8.0 min
   Pressure: 70 kPa
   MS Turbo Mass Perkin Elmer
   Solvent Delay 3.74 min
   SIR Scan, Mass 43, 70, 85
   3.75 to 8.0 min (EI+)
b) Preparation of the Formulations
2 g of each of the calcium carbonate samples was manually mixed with a spatula in a dish with 0.06 g of methylbutyl isovalerat.

100 ml hexadecane were placed into a dish on an electric stirring base. A magnet was placed in the dish and allowed to turn at a minimal rotation speed.

The pigment/methylbutyl isovalerat mixture was placed in the dish with the hexadecane to one side away from the stirrer. After a certain time period, a sample of the fluid phase was removed for analysis.

Figure 5:
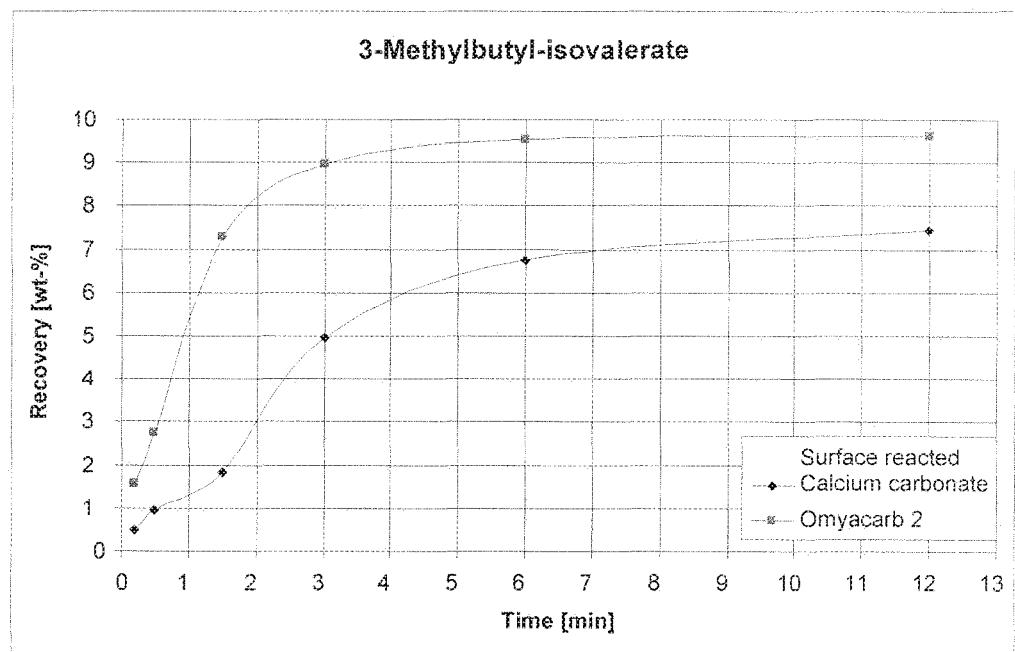
FIG. 5 shows a graph illustrating the sustained release effect of surface-treated calcium carbonate compared with conventional calcium carbonate

This process was repeated for increasing lengths of time, each time using a fresh calcium carbonate / methylbutyl isovalerat mixture.
c) Results and Discussion
The following table also showing the mixture weights as well as the time periods of the experiments, as well as FIG. 5 clearly illustrate the sustained release effect of surface-treated calcium carbonate compared with conventional calcium carbonate.

| | Sample 7 (Comparative) | | | | Sample 8 (Invention) | | | |
|---|---|---|---|---|---|---|---|---|
| Time [min] | Non surface-reacted CaCO$_3$ [g] | Methyl-butyl-iso-valerate [g] | Hexa-decane [ml] | Recovery | surface-reacted CaCO$_3$ [g] | Methyl-butyl-iso-valerate [g] | Hexa-decane [ml] | Recovery |
| 2 | 0.2003 | 0.0606 | 100.0 | 96 ppm (15.8 wt-%) | 0.2002 | 0.0624 | 100.0 | 30 ppm (4.8 wt-%) |
| 5 | 0.2009 | 0.0649 | 100.0 | 178 ppm (27.4 wt-%) | 0.2005 | 0.0628 | 100.0 | 59 ppm 9.4 wt-% |

-continued

| | Sample 7 (Comparative) | | | | Sample 8 (Invention) | | | |
|---|---|---|---|---|---|---|---|---|
| Time [min] | Non surface-reacted CaCO$_3$ [g] | Methyl-butyl-iso-valerate [g] | Hexa-decane [ml] | Recovery | surface-reacted CaCO$_3$ [g] | Methyl-butyl-iso-valerate [g] | Hexa-decane [ml] | Recovery |
| 15 | 0.2008 | 0.0625 | 100.0 | 455 ppm (72.8 wt-%) | 0.2001 | 0.0633 | 100.0 | 115 ppm 18.2 wt-% |
| 30 | 0.2007 | 0.0619 | 100.0 | 555 ppm (89.7 wt-%) | 0.2004 | 0.0606 | 100.0 | 300 ppm 49.5 wt-% |
| 60 | 0.2005 | 0.0612 | 100.0 | 585 ppm (95.6 wt-%) | 0.2006 | 0.0616 | 100.0 | 417 ppm 67.7 wt-% |
| 120 | 0.2002 | 0.0600 | 100.0 | 577 ppm (96.2 wt-%) | 0.2000 | 0.0640 | 100.0 | 476 ppm 74.4 wt-% |

Example 4

Further Formulations Comprising the Carrier of the Invention

1. Tooth Pastes a) Preparation of Surface-Reacted Calcium Carbonate

The surface-reacted calcium carbonate was prepared in a 5 m$^3$ reactor.

414 kg of dry natural calcium carbonate (undispersed marble) having a d$_{50}$ of 3 μm (Sedigraph) was filled into the vessel. Then water was added until a solids content of 15 wt.-% was obtained. The resulting slurry was heated to 70° C., then phosphoric acid (in the form of a 30% by mass solution) was added in an amount corresponding to 30 wt.-% dry/dry during 11 minutes, under stirring at 200 rpm. 5 minutes after the completion of the addition the temperature was decreased and the slurry filtered on a drum filter and then dried using a flash dryer.

The surface-reacted calcium carbonate used in the following example had
   a number mean particle size d$_{50}$ (Sedigraph) of 4.5 μm
   a rose-like surface structure
   a pH of 7.5 to 9.5
   a specific surface area as measured by BET: 40 m$^2$/g b) Material

| | Sample 9 | Sample 10 |
|---|---|---|
| Sorbitol 70% | 35.00 wt-% | 35.00 wt-% |
| Water | 29.60 wt-% | 38.60 wt-% |
| Sodium monofluorophosphate (Phoskadent NA 211 of BK-Gulini) | 1.10 wt-% | 1.10 wt-% |
| Potassium acesulfam (SUNETT of Nutrinova) | 0.10 wt-% | 0.10 wt-% |
| Calcium carbonate powder (Foodgrade limestone with d$_{50}$ = 3 μm of Omya AG) | 15.00 wt-% | 15.00 wt-% |
| Titanium dioxide powder (specific surface area of about 3.9 m$^2$/g) | 1.00 wt-% | 1.00 wt-% |
| surface-reacted calcium carbonate | 5.00 wt-% | 5.00 wt-% |
| Spearmint aroma | 0.80 wt-% | 0.80 wt-% |
| Cellulose gum | 1.40 wt-% | 1.40 wt-% |
| Sodium lauryl sulfate | 1.00 wt-% | 0.00 wt-% |
| Cocamidopropyl betaine | 0.00 wt-% | 2.00 wt-% |
| Water | 10.00 wt-% | 0.00 wt-% | c) Preparation of a Tooth Paste Formulation

Sorbitol, sodium monofluorophosphate, potassium acesulfam and water were thoroughly mixed together. To this mixture, a non surface reacted calcium carbonate powder/titanium dioxide powder blend was added and wetted therewith. Then, a mixture of surface-reacted calcium carbonate as described above and spearmint aroma, which was dropwise added to the surface reacted calcium carbonate while manually stirring, and, subsequently, cellulose gum were added while stirring in order to obtain a homogenous paste. The paste is further stirred slowly and cooled down to room temperature. Then, sodium lauryl sulphate in water/cocamidopropyl betaine is slowly added while stirring, under vacuum if required.

2. Skin Care Formulation

This example describes the loading of an oil in water emulsion into surface-reacted calcium carbonate acting as a carrier in a skin care formulation.

If the oil itself is loaded into the surface-reacted calcium carbonate, it would be displaced by water as soon as the loaded surface-reacted calcium carbonate is introduced into an aqueous formulation. Subsequently the oil would be visible as floating macroscopic droplets.

a) Preparation of Surface-Reacted Calcium Carbonate

The surface-reacted calcium carbonate was prepared in a 10 m$^3$ reactor.

1700 kg of dry natural calcium carbonate having a d$_{50}$ of 1.6 μm (Sedigraph) was filled into the vessel. Then, water was added until a solids content of 27 wt.-% was obtained. The resulting slurry was heated to 55° C., then phosphoric acid (in the form of a 35% by mass solution) was added in an amount corresponding to 13 wt.-% dry/dry during 20 minutes, under stirring at 100 rpm. 10 minutes after the completion of the addition the temperature was decreased and the slurry filtered on Sweco filter and then dried using a jet dryer.

The surface-reacted calcium carbonate used in the following example had
   a number mean particle size d$_{50}$ (Sedigraph) of 2.2 μm
   a rose-like surface structure
   a pH of 7.5 to 9.5
   a specific surface area as measured by BET: >25 m$^2$/g b) Preparation of a Skin Care Formulation First, an emulsion was prepared. This operation was carried out by using a rotor-stator dissolver from Kinematika, Polytron PT 300 at 10000 min$^{-1}$. For the preparation of the emulsion, 94.031 g of demineralised water was charged with 1.028 g of PEG-40 hydrogenated castor oil and homogenised until the emulsifier is well dissolved. Subsequently, 5.001 g of amaranth oil was added dropwise and dispersed well until a homogeneous milky emulsion was formed.

In a next step, the surface-reacted calcium carbonate was loaded with the resulting emulsion. For this step 15.004 g of surface-reacted calcium carbonate was weighed into a ceramic mortar (0 180 mm) and 20.209 g of the emulsion was added dropwise under mixing with pestle into the surface-reacted calcium carbonate until a white glossy creme was formed.

Then, the loaded surface-reacted calcium carbonate was blended with a gel formulation having the following composition:

| Gel formulation composition | |
|---|---|
| 1,2-Propanediol | 2.00 wt-% |
| 1,3-Butylene glycol | 3.00 wt-% |
| Ammonium acryloyldimethyltaurate/vinylpyrrolidone copolymer | 1.00 wt-% |
| Water | 66.82 wt-% |
| Lauryl PEG/PPG-18/18 Methicone (Dow Corning 5200 Formulation aid) | 0.50 wt-% |
| PEG-12 Dimethicone (Dow Corning 5329 Emulsifier) | 4.00 wt-% |
| *Butyrospermum Parkii* (Shea butter) and dimethicone (and) Ceteth-20 (and) Steareth-21 (Dow Corning 7-3121 Shea Blend Emulsion) | 8.00 wt-% |
| Dimethicone/Vinyl Dimethicone Crosspolymer (and) C12-14 pareth-12 (Dow Corning 9509 Silicone Elastomer Suspension) | 5.00 wt-% |
| Water (and) Alcohol (and) Lecithin (and) Caffeine (and) Carnitine (and) *Centella asiatica* (and) Potassium Phosphate (and) Sodium Hydroxide (and) Theobromine (Dow Corning DS-2007 Modeling Liposome) | 5.00 wt-% |
| Divinyldimethicone/Dimethicone Copolymer(and) C12-13 Pareth-23 (and) C12-13 Pareth-3 (Dow Corning HMW 2220 non-ionic emulsion) | 2.00 wt-% |
| Phenoxyethanol (and) Methylparaben (and) Ethylparaben (and) Butylparaben (and) Propylparaben (and) Isobutylparaben (Phenochem; SLI Chemicals GmbH) | 1.00 wt-% |
| 25% menthyl lactate solution in ethanol | 1.60 wt-% |
| Sodium hydroxide (10% solution) | 0.08 wt-% |

The gel formulation was prepared by mixing 1,2-propanediol, butylene glycol and water, subsequent interspersing under stirring ammonium acryloyldimethyltaurate/VP Copolymer and allowing swelling resulting in a gel. Then, Lauryl PEG/PPG-18/18 Methicone, PEG-12 Dimethicone, Shea Blend Emulsion, Silicone Elastomer Suspension, Liposome, non-ionic emulsion and Phenochem were mixed under stirring and added to the gel. To this emulsion gel the mixture of 25% menthyl lactate solution in ethanol and 10% sodium hydroxide solution was added, and the resulting gel was quickly and intensively homogenized and stirred for another 15 minutes.

For obtaining the skin care formulation, 20 g of the loaded surface-reacted calcium carbonate was blended manually with 100 g of the gel formulation until a homogenous white glossy creme was formed.

The resulting creme had
a pH of 6.94
a Brookfield viscosity of 23480 mPa·s (Brookfield DV-11 (RT; RV 5, 30 s/10 rpm))

The invention claimed is:
1. A method for preparing a loaded carrier comprising the steps of:
   (a) providing surface reacted calcium carbonate in powder or granule form that is reaction product of calcium carbonate with carbon dioxide and one or more acids in an aqueous environment, wherein the carbon dioxide is formed in situ by the acid treatment and/or is supplied from an external source,
   (b) providing an active agent in the form of a prepared solution or suspension;
   (c) contacting the surface reacted calcium carbonate with the active agent until a sufficient amount of the active agent is adsorbed onto and/or absorbed into the surface-reacted calcium carbonate; and
   (d) separating the loaded carrier from excess solution or suspension.

2. The method according to claim 1, wherein the calcium carbonate is natural calcium carbonate selected from the group consisting of marble, calcite, chalk, limestone, and any mixture thereof.

3. The method according to claim 1, wherein the one or more acids is selected from the group consisting of hydrochloric acid, sulphuric acid, sulphurous acid, hydrosulphate, phosphoric acid, oxalic acid, and any mixture thereof.

4. The method according to claim 1, wherein the one or more acids is phosphoric acid.

5. The method according to claim 1, wherein the surface reacted calcium carbonate has a specific surface area of from 5 $m^2$/g to 200 $m^2$/g, measured using nitrogen and the BET method according to ISO 9277.

6. The method according to claim 1, wherein the surface reacted calcium carbonate has a specific surface area of from 20 $m^2$/g to 80 $m^2$/g, measured using nitrogen and the BET method according to ISO 9277.

7. The method according to claim 1, wherein the surface reacted calcium carbonate has a specific surface area of from 30 $m^2$/g to 60 $m^2$/g, measured using nitrogen and the BET method according to ISO 9277.

8. The method according to claim 1, wherein the surface reacted calcium carbonate has a weight median grain diameter $d_{50}$ of from 0.1 to 50 µm, measured according to the sedimentation method.

9. The method according to claim 1, wherein the surface reacted calcium carbonate has a weight median grain diameter $d_{50}$ of from 0.5 to 25 µm, measured according to the sedimentation method.

10. The method according to claim 1, wherein the surface reacted calcium carbonate has a weight median grain diameter $d_{50}$ of from 0.8 to 20 µm, measured according to the sedimentation method.

11. The method according to claim 1, wherein the surface reacted calcium carbonate has an intra-particle porosity determined as a pore volume per unit particle volume from 20 vol.-% to 99 vol.-%, calculated from a mercury porosimetry measurement.

12. The method according to claim 1, wherein the surface reacted calcium carbonate has an intra-particle porosity determined as a pore volume per unit particle volume from 30 vol.-% to 70 vol.-%, calculated from a mercury porosimetry measurement.

13. The method according to claim 1, wherein the surface reacted calcium carbonate has an intra-particle porosity determined as a pore volume per unit particle volume from 40 vol.-% to 60 vol.-%, calculated from a mercury porosimetry measurement.

14. The method according to claim 1, wherein the loaded carrier is combined with one or more cosmetically acceptable carriers to obtain a cosmetic formulation in the form of a powder, a cream, an emulsion, a gel, a paste, a soap, a gum, or a tablet.

15. The method according to claim 14, wherein the one or more active agents is selected from the group consisting of a pharmaceutical active agent, a biological active agent, a scented agent, a flavoring agent, a biocide, a disinfecting agent, a surfactant, a defoamer, a softener, a mineral oil, a wetting agent, a wax, a hydrolytic agent, and an anti-dusting oil.

16. The method according to claim 14, wherein the one or more active agents is selected from the group consisting of triclosan, limonene, peppermint, silicon, paraffin, o-phenylphenol and Bronopol.

17. The method according to claim 14, wherein the cosmetic formulation is a lipstick, a foundation, a deodorant, a sunscreen, a skin care formulation, a hair care product, a soap, a skin cream, a tooth paste, a bath additive, a foot powder, a facial powder, a sun screen, or a chewing gum.

18. The method according to claim 1, wherein the loaded carrier is combined with one or more pharmaceutically acceptable carriers to obtain a pharmaceutical formulation in the form of a capsule, a tablet, a patch, or a cream.

19. The method according to claim 1, wherein the loaded carrier is combined with one or more pharmaceutically acceptable carriers to obtain a pharmaceutical formulation in the form of a capsule, a tablet, a patch, or a cream.

20. The method according to claim 1, wherein the loaded carrier is formulated into an agricultural formulation, and wherein the one or more active agents is selected from the group consisting of an agricultural agent, a biocide, a pesticide, and a herbicide.

\* \* \* \* \*